United States Patent
Karamanoglu et al.

(10) Patent No.: US 8,211,028 B2
(45) Date of Patent: Jul. 3, 2012

(54) SYSTEM AND METHOD OF DETERMINING ARTERIAL BLOOD PRESSURE AND VENTRICULAR FILL PARAMETERS FROM VENTRICULAR BLOOD PRESSURE WAVEFORM DATA

(75) Inventors: Mustafa Karamanoglu, Fridley, MN (US); Tommy D. Bennett, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 1099 days.

(21) Appl. No.: 12/112,544

(22) Filed: Apr. 30, 2008

(65) Prior Publication Data

US 2009/0275843 A1   Nov. 5, 2009

(51) Int. Cl.
*A61B 5/02* (2006.01)
(52) U.S. Cl. ...................................... 600/485
(58) Field of Classification Search ............... None
See application file for complete search history.

(56) References Cited

U.S. PATENT DOCUMENTS

| | | |
|---|---|---|
| 5,368,040 A | 11/1994 | Carney |
| 5,626,623 A | 5/1997 | Kieval et al. |
| 6,580,946 B2 | 6/2003 | Struble |
| 6,865,419 B2 | 3/2005 | Mulligan et al. |
| 2004/0167410 A1 | 8/2004 | Hettrick |
| 2006/0094967 A1 | 5/2006 | Bennett et al. |
| 2006/0167361 A1 | 7/2006 | Bennett et al. |
| 2007/0219591 A1 | 9/2007 | Zdeblick et al. |

OTHER PUBLICATIONS

PCT International Search Report, PCT/US2009/039402, 5 pgs.

*Primary Examiner* — Tracy Vivlemore
(74) *Attorney, Agent, or Firm* — Reed A. Duthler; Stephen W. Bauer (57) ABSTRACT

A system and method of determining hemodynamic parameters uses sensed ventricular blood pressure during a portion of ventricular pressure waveform following peak pressure. An estimated arterial diastolic pressure is based upon an amplitude of the sensed ventricular pressure corresponding to a time at which a first derivative of ventricular pressure as a function of time is at a minimum ($dP/dt_{min}$). Fill parameters such as isovolumetric relaxation constant, ventricular suction pressure, atrial kick pressure, and transvalve pressure gradient are derived from measured pressures representing minimum ventricular pressure, ventricular diastolic pressure, and diastasis pressure.

15 Claims, 5 Drawing Sheets

SYSTEM AND METHOD OF DETERMINING ARTERIAL BLOOD PRESSURE AND VENTRICULAR FILL PARAMETERS FROM VENTRICULAR BLOOD PRESSURE WAVEFORM DATA

BACKGROUND OF THE INVENTION

The present invention relates to hemodynamic monitoring devices and methods. In particular, the invention relates to a determination of blood pressure in pulmonary and systemic arteries and derivation of ventricular fill parameters based upon measurements of pressure within chambers of the heart.

The blood pressure in the pulmonary arteries and systemic arteries is important for assessing function of the heart, diagnosing hypertension, titrating drug treatment, and treating patients and animals under a wide variety of pathological and physiological conditions. If blood pressure measurements are done within chambers of the heart, the absolute diastolic pressures in the arteries can be difficult to estimate.

Systems and methods have been developed to derive an estimated pulmonary artery diastolic pressure (ePAD) based upon ventricular pressure measured within the right ventricle. The ePAD pressure has been determined as being equal to the right ventricular pressure signal amplitude at the time of the maximum rate of rise in right ventricular pressure ($dP/dt_{max}$).

The ePAD pressure value can then be used, along with an estimated systolic pressure corresponding to the peak right ventricular pressure, to derive other estimated values, such as mean pulmonary artery pressure (MPAP). Systems using ePAD pressure values are described, for example, in Bennett et al. U.S. Published Application No. US 2006/0167361; Bennett et al. U.S. Published Application No. US 2006/0094967; Mulligan et al. U.S. Pat. No. 6,865,419; Struble U.S. Pat. No. 6,580,946; Kieval et al. U.S. Pat. No. 5,626,623; and Carney U.S. Pat. No. 5,368,040, each of which are hereby incorporated by reference in their entirety.

BRIEF SUMMARY OF THE INVENTION

Hemodynamic monitoring devices and methods that measure ventricular blood pressure can use sensed blood pressure during a fill portion of the ventricular blood pressure waveform following peak pressure to derive hemodynamic parameters. These hemodynamic parameters may include estimated parameters relating to the pulmonary artery or the aorta, as well as parameters relating to ventricular fill characteristics.

In another aspect, the present invention is based upon the discovery that diastolic pressure in the pulmonary artery (PAD) or in the aorta (AoD) can be estimated by the ventricular pressure at the time that the time rate of change of ventricular pressure is at a peak minimum ($dP/dt_{min}$). Based upon this discovery, an estimation of arterial diastolic pressure (ePAD or eAOD) is made using sensed ventricular pressure by producing a ventricular pressure waveform, deriving a first derivative of the ventricular pressure waveform, and deriving an estimated arterial diastolic pressure based upon ventricular pressure amplitude at the time at which dP/dt is a peak minimum. To derive estimated pulmonary artery diastolic (ePAD) pressure, right ventricular pressure is sensed. To derive estimated aortic diastolic (eAOD) pressure, left ventricular pressure is sensed.

In another aspect, the present invention makes use of pressure measurements that occur between $dP/dt_{min}$ and a next occurrence of a beginning of a new ventricular pumping cycle (such as an R-wave). Pressure values are derived from the waveform representing a minimum ventricular pressure, a ventricular end diastolic pressure, and a diastasis pressure. From those pressure values, other parameters may be derived, including an isovolumetric relaxation time constant, a ventricular suction pressure, an atrial kick pressure, and a trans-valve gradient pressure.

In another aspect, hemodynamic parameters are derived from pressure measurements made within the left ventricle. The parameters include estimated aortic systolic, diastolic, and mean pressures, pre-ejection interval, systolic time interval, ejection duration, and left ventricular filling parameters.

DETAILED DESCRIPTION

Figure 1:
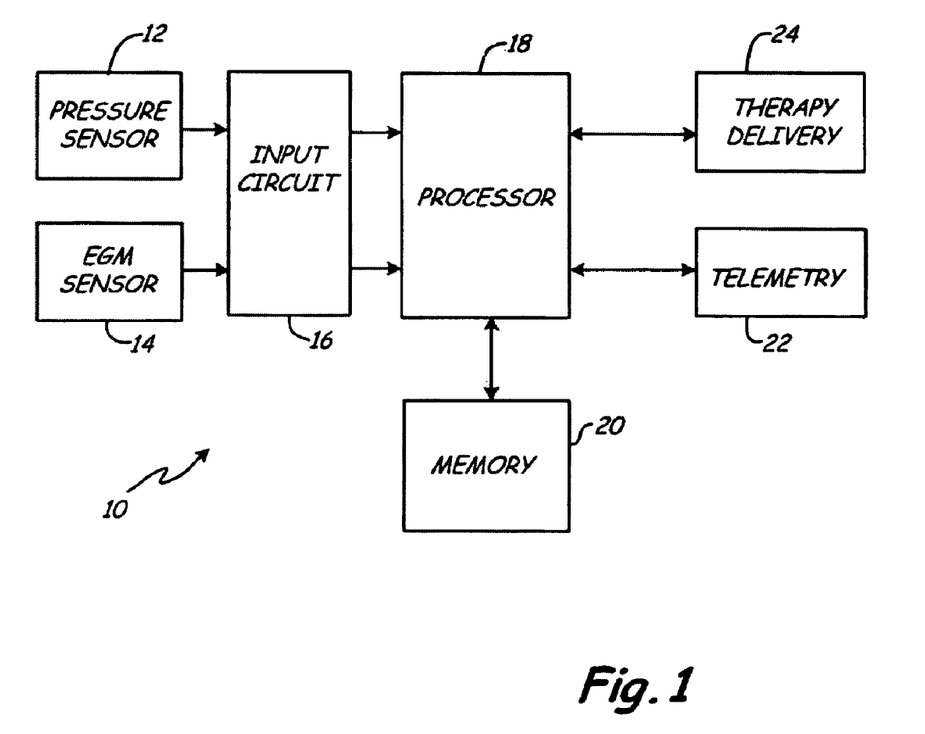
FIG. 1 is a block diagram of an implantable medical device for measuring ventricular pressure and deriving blood pressure data related to pulmonary or systemic arteries, as well as ventricular filling parameters.

FIG. 1 is a block diagram of implantable medical device (IMD) 10 for chronically monitoring cardiac performance in a patient. IMD 10 includes pressure sensor 12, electrogram (EGM) sensor 14, input circuit 16, processor 18, memory 20, telemetry circuit 22, and therapy delivery circuit 24.

Pressure sensor 12 is located inside either the right ventricle or the left ventricle of a patient's heart to sense blood pressure. EGM sensor 14 is located in or hear the heart to sense electrical activity of the heart.

Input circuit 16 is the signal processing circuit that receives pressure signal representative of blood pressure in the ventricle as a function of time from pressure sensor 12, and receives an electrical signal representative of electrical activity of the heart as a function of time from EGM sensor 14. Input circuit 16 may sample, demodulate, or otherwise process the signals received from pressure sensor 12 and EGM sensor 14.

From these processed pressure and EMG signals received from input circuit 16, processor 18 derives several fiducials and hemodynamic parameters. The hemodynamic parameters may be stored at processor 18 in memory 20 on a beat-by-beat basis, minute-to-minute basis, hour-to-hour basis, or some other basis.

Memory 20 may also include nonvolatile memory used to store code used to define the functions performed by processor 18, as well as configuration data used by processor 18.

Processor 18 may communicate the derived hemodynamic parameters externally through telemetry circuit 22. Processor 18 may also receive information from a user, such as a physician or other medical personnel, through telemetry circuit 22.

In some embodiments, IMD 10 delivers therapy in addition to monitoring hemodynamic parameters. Processor 18 may provide the therapy control signal to therapy delivery circuit 24 to adjust or titrate any of the various therapies being administered to the patient based upon the hemodynamic parameters derived.

Figure 2:
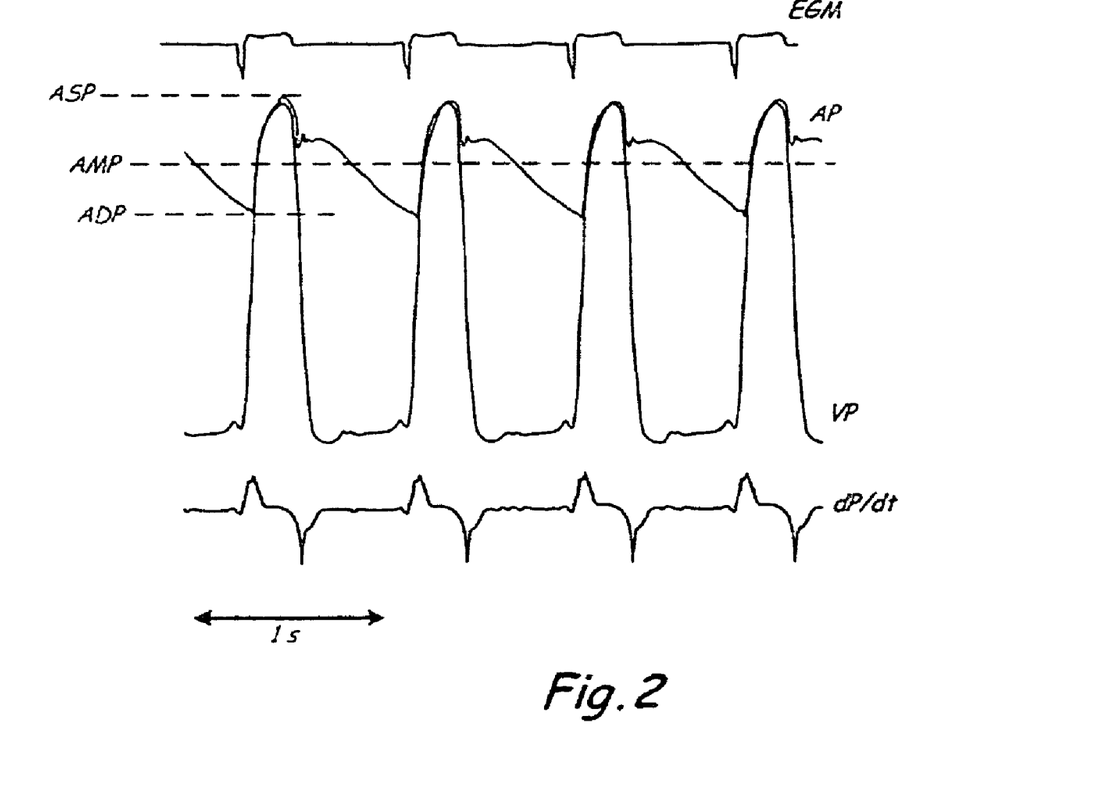
FIG. 2 is a diagram showing electrogram (EGM), arterial pressure (AP), ventricular pressure (VP), and first derivative (dP/dt) waveforms.

FIG. 2 is a diagram showing an electrogram (EGM) waveform, an arterial pressure (AP) waveform, a ventricular pressure (VP) waveform, and a first derivative (dP/dt) waveform. The VP waveform can be generated by pressure sensor 12 located in either the patient's right ventricle or left ventricle. The EGM waveform is produced by EGM sensor 14. Either input circuit 16, or processor 18 can produce the dP/dt waveform by taking the first derivative of the VP waveform. The arterial pressure AP waveform, however, is not directly sensed, and is not available to processor 18. However, estimates of arterial systolic pressure ASP, diastolic pressure ADP, and arterial mean pressure AMP can be derived by processor 18 using the EGM, VP, and dP/dt waveforms.

Figure 3:
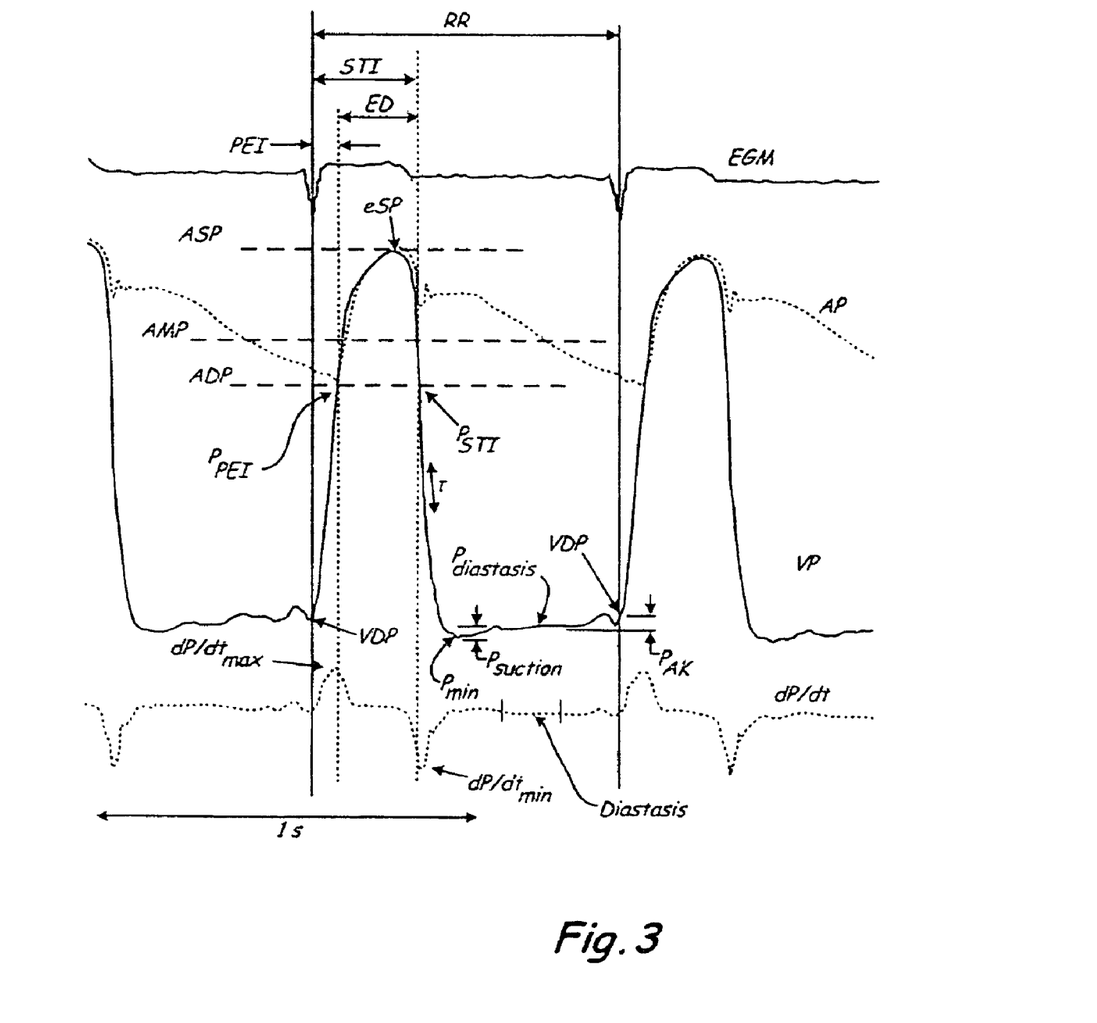
FIG. 3 shows the EGM, AP, VP, and dP/dt waveforms of FIG. 2 on a larger scale with associated fiducial points and derived hemodynamic parameters identified.

FIG. 3 is a diagram showing the EGM, AP, VP, and dP/dt waveforms of FIG. 2 on a larger scale. Also shown in FIG. 3 are associated fiducial points and derived hemodynamic parameters.

In FIG. 3, a first fiducial point is derived from the EGM waveform. It represents the occurrence of an R-wave. The time interval between successive R-waves (RR) is also shown in FIG. 3.

A second fiducial point is the occurrence of the maximum value of dP/dt ($dP/dt_{max}$). The $dP/dt_{max}$ fiducial point occurs during the rising portion of the VP waveform.

The time interval between the first fiducial point (an R-wave) and the second fiducial point ($dP/dt_{max}$) is the pre-ejection interval (PEI).

A third fiducial point occurs when dP/dt is a minimum ($dP/dt_{min}$). This occurs on the trailing edge of the VP signal, after a peak ventricular pressure has been obtained. The time from the first fiducial point to the third fiducial point represents the systolic time interval (STI) shown in FIG. 3. The ejection duration (ED) is the time difference between the pre-ejection interval (PEI) and the systolic time interval (STI), or the time between the second fiducial point and the third fiducial point. All three parameters PEI, STI, and ED can be derived by processor 18 using the pressure waveform and the fiducials.

As shown in FIG. 3, arterial systolic pressure (ASP) is essentially the same as the ventricular systolic pressure. An estimated systolic pressure (eAoSP) of the aorta can be defined as being equal to the maximum value of the left ventricular pressure. An estimated systolic pressure of the pulmonary artery (ePASP) can be defined as being equal to the maximum value of the right ventricular pressure.

As shown in FIG. 3, the second fiducial point ($dP/dt_{max}$) occurs close in time to the minimum of the arterial pressure (AP) waveform, which represents the arterial diastolic pressure. FIG. 3 also shows that the ventricular pressure at the second fiducial point is relatively close to the arterial diastolic pressure. It is possible, therefore, to use ventricular pressure at the second fiducial point ($dP/dt_{max}$) as an estimated arterial diastolic pressure ($P_{PEI}$). This is similar to use of right ventricular pressure at $dP/dt_{max}$ as an estimated pulmonary artery diastolic pressure (ePAD), as described, for example, in Bennett et al. US 2006/0094967; Bennett et al US 2006/0167361; and Mulligan et al. U.S. Pat. No. 6,865,419.

As shown in FIG. 3, the arterial pressure (AP) waveform exhibits a pressure at the third fiducial point that is much higher than the diastolic pressure in the artery, which represents the minimum in the AP waveform. It has been discovered, however, that the use of ventricular pressure at the third fiducial point corresponding to $dP/dt_{min}(P_{STI})$ provides another accurate estimation of arterial diastolic pressure. This discovery applies to the estimation of both aortic diastolic pressure (AoDP) using a sensed left ventricular pressure waveform, or estimation of pulmonary artery diastolic (ePAD) pressure using a sensed right ventricular pressure waveform.

Figure 4A:
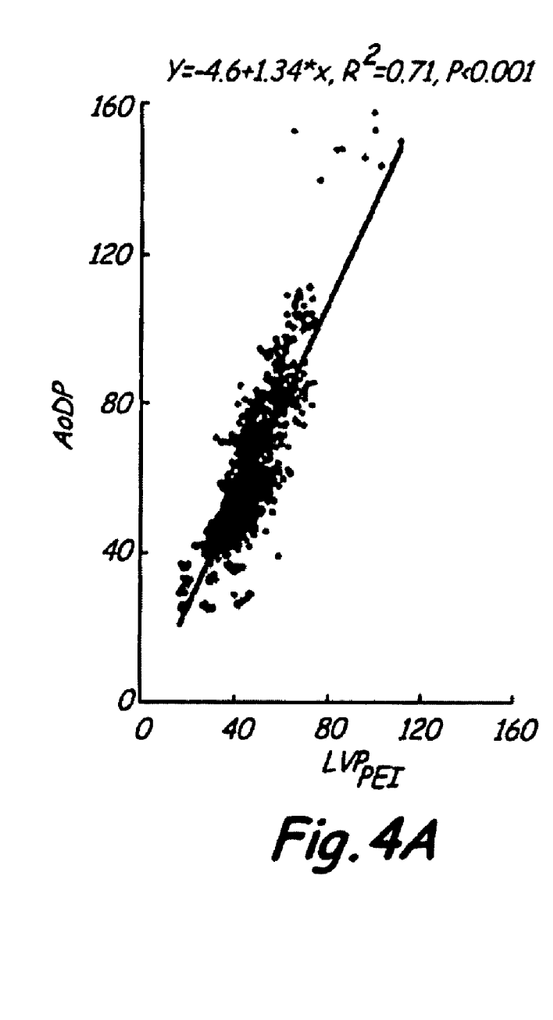
FIG. 4A shows measured aortic diastolic pressure versus estimated aortic diastolic pressure based upon left ventricular pressure at $dP/dt_{max}$.

FIG. 4A shows a plot showing the relationship of measured and estimated aortic pressure, where estimated aortic diastolic pressure (AoDP) was based upon left ventricular pressure ($LVP_{PEI}$) at the second fiducial point ($dP/dt_{max}$). Measured aortic diastolic pressure (AoDP) is plotted along the vertical (Y) axis, and estimated aortic diastolic pressure ($LVP_{PEI}$) is plotted along the horizontal axis. The position of each data point represents an $LVP_{PEI}$ and the corresponding ADP. The relationship shown in FIG. 4A is defined by the equation $AoDP=aLVP_{PEI}+b$. By way of example, for this patient population, the coefficient b was −4.6 and the coefficient a was 1.34 where Y is the measured aortic diastolic pressure and X is estimated aortic diastolic pressure $LVP_{PEI}$, which is derived using the second fiducial point $dP/dt_{max}$. As shown in FIG. 4A, a statistical analysis of the data yields $R^2=0.71$, and $P<0.001$.

Figure 4B:
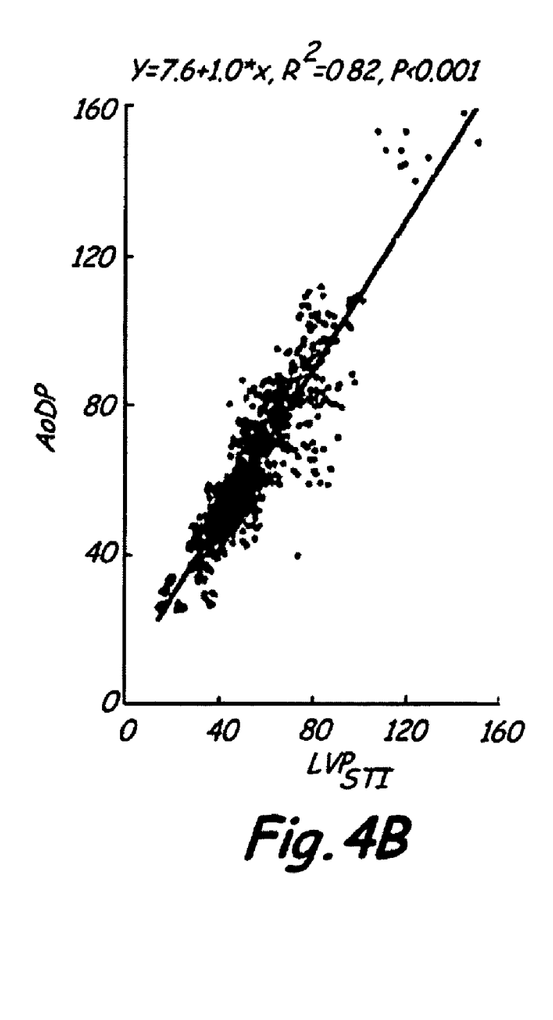
FIG. 4B shows measured aortic diastolic pressure versus estimated aortic diastolic pressure based upon left ventricular pressure at $dP/dt_{min}$.

FIG. 4B shows a similar plot showing the relationship between actual aortic diastolic pressure ADP and estimated aortic diastolic pressure eAOD based upon the left ventricular pressure at the third fiducial point $dP/dt_{min}$. The relationship is defined by $ADP=aLVP_{STI}+b$. By way of example, for this patient population the coefficient b was 7.6 and the coefficient a was 1. In this case, $R^2=0.82$ and $P<0.001$. Thus, the use of pressure at the third fiducial point $dP/dt_{min}$ for $LVP_{STI}$ represents statistically a more accurate estimation of the actual aortic diastolic pressure AoDP.

Figure 5A:
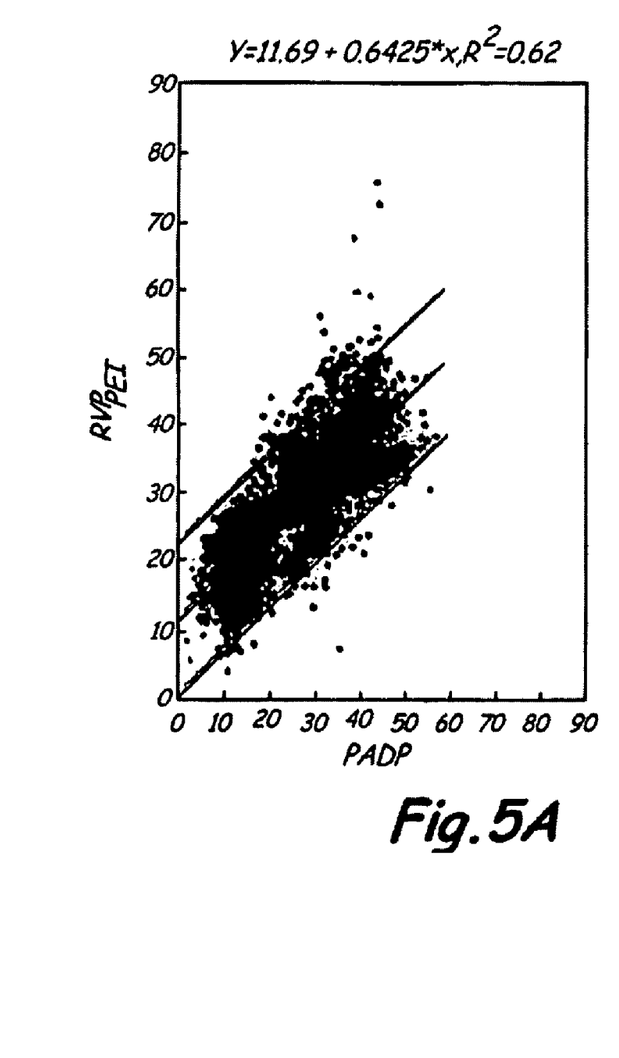
FIG. 5A is a graph showing estimated pulmonary artery diastolic pressure based upon right ventricular pressure at $dP/dt_{max}$ versus measured pulmonary artery diastolic pressure.
Figure 5B:
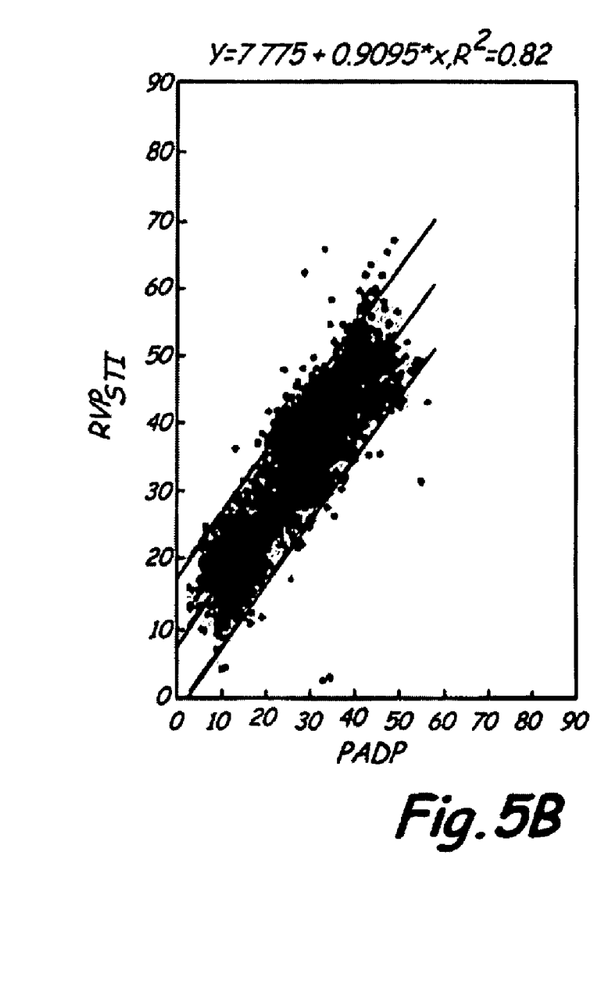
FIG. 5B shows estimated pulmonary artery diastolic pressure based upon right ventricular pressure at $dP/dt_{min}$ versus measured pulmonary diastolic pressure.

FIGS. 5A and 5B show a similar result achieved by estimating pulmonary artery diastolic pressure using right ventricular pressure at $dP/dt_{min}$ and $dP/dt_{max}$.

In FIG. 5A, $RVP_{PEI}$ is plotted along the vertical (Y) axis, and measured pulmonary artery diastolic pressure is plotted along the horizontal (X) axis. $RVP_{PEI}$ represents the right ventricular pressure at $dP/dt_{max}$, which is the traditional way that estimated pulmonary artery diastolic pressure has been derived. The relationship between the estimated and actual pulmonary artery diastolic pressure is shown by the relationship $RVP_{PEI}=aPADP+b$. By way of example, for this patient population the coefficient b was 11.69 and the coefficient a was 0.6425. In this case, $R^2=0.62$.

FIG. 5B shows a similar plot with $RVP_{PEI}$ along the vertical axis and actual pulmonary artery diastolic pressure PADP along the horizontal axis. The relationship is defined by $RVP_{PEI}=aPADP+b$. By way of example, for this patient population the coefficient b was 7.775 and the coefficient a was 0.9095. In this case, $R^2=0.82$, which indicates that right ventricular pressure at the third fiducial point $dP/dt_{min}$ ($RVP_{STI}$) is a more accurate estimation of pulmonary artery diastolic pressure PADP.

As illustrated by both FIGS. 4A and 4B and FIGS. 5A and 5B, the use of ventricular pressure at the $dP/dt_{min}$ third fiducial point provides another accurate estimation of arterial (i.e. either pulmonary or aortic) diastolic pressure ADP.

In either case, an estimated arterial mean pressure eAMP can then be derived by processor 18 using estimated arterial systolic pressure eASP, estimated arterial diastolic pressure eADP, and intervals STI and RR. The relationship can be stated as: eAMP=eDP+(eSP−eDP)*STI/RR.

Processor 18 may also derive other hemodynamic values may be derived from pressure waveform data contained in the portion of the waveform following the pressure peak. The time between third fiducial point $dP/dt_{min}$ and the first fiducial point representing the next R-wave represents a time period during which the ventricle is filling. Processor 18 can derive, from the VP waveform between the third fiducial point and the following first fiducial point, parameters related to ventricular filling properties. Some of these parameters (depicted in FIG. 3) include isovolumetric relaxation time constant tau ($\tau$), ventricular suction $P_{suction}$, atrial kick pressure $P_{AK}$, diastasis pressure $P_{diastasis}$, and transmitral pressure gradient $P_{mitral}$.

Processor 18 uses the third fiducial point derived from the dP/dt waveform and the first fiducial point derived from the EGM waveform to define a fill portion of the ventricular pressure waveform which begins with the third fiducial point and ends with the next first fiducial point. Within that fill portion, processor 18 identifies a minimum pressure $VP_{min}$ and a ventricular end diastolic pressure VDP which corresponds to the ventricular pressure at the R-wave (first fiducial point). The pressure at $dP/dt_{min}$ ($P_{STI}$) and at VDP can then be used along with $dP/dt_{min}$ to derive the isovolumetric relaxation time constant tau (9) as:

$$\tau = -(P_{STI}-VDP)/dP/dt_{min}.$$

Processor 18 also identifies a diastasis portion of the VP waveform by using the dP/dt waveform. The diastasis portion is a portion of the VP waveform between $VP_{min}$ and VDP which the waveform is relatively flat. This corresponds to dP/dt being essentially zero. The pressure during this diastasis portion ($P_{diastasis}$) can then be used along with $VP_{min}$ and VDP to derive ventricular fill parameters. The difference between $P_{diastasis}$ and $VP_{min}$ is the ventricular suction pressure $P_{suction}$. In other words:

$$P_{suction}=P_{diastasis}-VP_{min}.$$

The difference between VDP and the diastasis pressure $P_{diastasis}$ represents the pressure contribution of the atrial kick $P_{AK}$. In other words:

$$P_{AK}=VDP-P_{diastasis}.$$

During the filling portion, the mitral valve between the left atrium and the left ventricle opens and blood flows from the left atrium into the left ventricle. The filling can be aided by suction of the left ventricle as well as pushing of the blood into the left ventricle by the left atrium (i.e. the atrial kick).

The use of parameters derived from the LVP waveform during the filling portion allows processor 18 to provide an indication of the amount of effort being generated, and whether that effort is ventricular suction or atrial pushing.

If there is mitral stenosis, (i.e. the opening through the mitral valve is reduced), the left ventricle will require a greater amount of sucking in order to draw blood through the smaller orifice. Thus the value of $P_{suction}$ can provide an indication of the amount of sucking effort being provided by the left ventricle, which may be related to the condition of the mitral valve.

A large left atrial kick is an indication of high left atrial pressures occurring. This may provide an indicator of potential pulmonary edema. In another case, processor 18 may determine that the left atrium is beating erratically by analyzing the filling parameters. This may be an indication that synchronization of the left atrium to the left ventricle filling is an issue, and that cardiac resynchronization may be needed.

Processor 18 can derive a transmitral pressure gradient value based upon a difference between the left ventricular end diastolic pressure LVDP and the minimum left ventricular pressure $LVP_{min}$:

$$P_{mitral}=LVDP-LVP_{min}=P_{suction}+P_{AK}.$$

The transmittal pressure gradient, therefore, is equal to the sum of the ventricular suction $P_{suction}$ and the atrial kick pressure $P_{AK}$.

During the filling portion, the tricuspid valve between the right atrium and the right ventricle opens and blood flows from the right atrium into the right ventricle. The filling can be aided by suction of the right ventricle as well as pushing of the blood into the right ventricle by the right atrium (i.e. the atrial kick).

The use of parameters derived from the RVP waveform during the filling portion allows processor 18 to provide an indication of the amount of effort being generated, and whether that effort is ventricular suction or atrial pushing.

If there is tricuspid stenosis, (i.e. the opening through the tricuspid valve is reduced), the right ventricle will require a greater amount of sucking in order to draw blood through the smaller orifice. Thus the value of $P_{suction}$ can provide an indication of the amount of sucking effort being provided by the right ventricle, which may be related to condition of the tricuspid valve.

A large right atrial kick is an indication of high right atrial pressures occurring. This may provide an indicator of potential central venous edema. In another case, processor 18 may determine that the right atrium is beating erratically by analyzing the filling parameters. This may be an indication that synchronization of the right atrium to the right ventricle filling is an issue, and that AV resynchronization may be needed.

$$P_{tricuspid}=RVDP-RVP_{min}=P_{suction}+P_{AK}.$$

The transtricuspid pressure gradient, therefore, is equal to the sum of the right ventricular suction $P_{suction}$ and the right atrial kick pressure $P_{AK}$.

Processor 18 may also make use of the ventricular pressure rise and decay, as indicated by $dP/dt_{max}$ and $dP/dt_{min}$ to provide an estimate of ventricle muscle performance. This information, together with a fill characteristics and the arterial pressure parameters derived can be stored and then reported via telemetry. In addition, if the parameters indicate a condition requiring medical intervention, an alarm can be provided through by sending a signal via telemetry to an external alarm device, or through an alarm (such as a sound or vibration transducer) associated with the IMD 10.

The derived parameters can also be used to control therapy being delivered by IMD 10 to a patient. This may involve adjusting pacing therapy to one or more chambers of the heart, or may involve titrating drug treatment being delivered through an implanted pump that is a part of or associated with IMD 10.

The following numbered examples are intended as illustrative and not limiting as to the subject matter covered by the foregoing description and the following claims.

EXAMPLES

1. An implantable medical device comprising:
    an input circuit that receives a pressure waveform signal representative of a pressure (P) sensed within a ventricle of a patient's heart as a function of time (t); and
    a processor that derives from the pressure waveform signal at least one hemodynamic parameter based upon at least one ventricular pressure value during a portion of the pressure waveform signal between a peak ventricular pressure and a beginning of a next ventricular pumping cycle.

2. An implantable medical device according to claim 1, wherein the processor derives an estimated arterial diastolic pressure based upon pressure in the ventricle at a time corresponding to a maximum rate of pressure decline ($dP/dt_{min}$).

3. An implantable medical device according to claim 1 and further comprising a blood pressure sensor located in the ventricle for providing the pressure waveform signal to the input circuit.

4. An implantable medical device according to claim 3, wherein the blood pressure sensor is a right ventricular pressure sensor, and the estimated arterial diastolic pressure is an estimated pulmonary artery diastolic pressure.

5. An implantable medical device according to claim 3, wherein the blood pressure sensor is a left ventricular pressure sensor, and the estimated arterial diastolic pressure is an estimated aortic diastolic pressure.

6. An implantable medical device according to claim 1, wherein the input circuit also receives an electrical signal representative of electrical activity in the heart as a function of time.

7. An implantable medical device according to claim 1, wherein the processor derives from the pressure waveform signal at least one ventricular fill parameter based upon pressure values during a fill portion between occurrence of $dP/dt_{min}$ and the beginning of a next ventricular pumping cycle.

8. An implantable medical device according to claim 7, wherein the processor derives at least one ventricular fill parameter by:
producing a dP/dt waveform from the pressure signal;
identifying a fill portion of the pressure waveform signal;
identifying a diastasis portion of the fill portion using the dP/dt waveform; and
deriving a diastasis pressure representing the ventricular pressure in the diastasis portion of the pressure waveform signal.

9. An implantable medical device according to claim 7, wherein the processor determines from the fill portion of the pressure waveform signal a ventricular diastolic pressure, a minimum ventricular pressure, and a diastasis pressure.

10. An implantable medical device according to claim 9 wherein the processor derives an atrial kick parameter based upon a difference between the ventricular end diastolic pressure and the diastasis pressure.

11. An implantable medical device according to claim 9, wherein the processor derives a ventricular suction parameter based upon a difference between the diastasis ventricular pressure and the minimum ventricular pressure.

12. An implantable medical device according to claim 9, wherein the processor derives a transvalve pressure gradient parameter based upon a difference between the ventricular diastolic pressure and the minimum ventricular pressure.

13. An implantable medical device according to claim 1, wherein the process derives an isovolumetric relaxation constant based upon $dP/dt_{min}$, a ventricular pressure at $dP/dt_{min}$ ($P_{STI}$), and a ventricular pressure at occurrence of an R-wave (VDP).

14. A method comprising:
sensing ventricular blood pressure to produce a ventricular pressure waveform; and
deriving at least one hemodynamic parameter based upon at least one ventricular pressure during a portion of the ventricular pressure waveform between a peak ventricular pressure and a beginning of a next ventricular pumping cycle.

15. A method according to claim 14, wherein deriving at least one hemodynamic parameter comprises:
deriving an estimated arterial diastolic pressure based upon ventricular pressure amplitude at a time when $dP/dt_{min}$ occurs.

16. A method according to claim 15, wherein the ventricular blood pressure is sensed by a blood pressure sensor located in a ventricle.

17. A method according to claim 16, wherein the ventricle is a right ventricle, and the estimated arterial diastolic pressure is an estimated pulmonary artery diastolic pressure.

18. A method according to claim 16, wherein the ventricle is a left ventricle and the estimated arterial diastolic pressure is an estimated aortic diastolic pressure.

19. A method according to claim 15 and further comprising:
deriving an estimated arterial systolic pressure based upon a maximum sensed ventricular blood pressure.

20. A method according to claim 19, and further comprising:
deriving an estimated mean arterial pressure based upon the estimated arterial systolic pressure and the estimated arterial diastolic pressure.

21. A method according to claim 14, wherein deriving at least one hemodynamic parameter comprises:
deriving, from at least two ventricular pressure values during a fill portion of the ventricular pressure waveform, at least one ventricular fill parameter.

22. A method according to claim 21, wherein deriving at least one ventricular fill parameter comprises:
producing a dP/dt waveform representing a first derivative of the ventricular pressure waveform;
identifying a fill portion of the ventricular pressure waveform;
identifying a diastasis portion of the fill portion using the dP/dt waveform; and
deriving a diastasis pressure representing the ventricular pressure in the diastasis portion of the ventricular pressure waveform.

23. A method according to claim 21, wherein deriving at least one ventricular fill parameter comprises:
determining a ventricular end diastolic pressure within the fill portion;
determining a diastasis pressure within the fill portion; and
deriving an atrial kick parameter based upon a difference between the ventricular end diastolic pressure and the diastasis pressure.

24. A method according to claim 21, wherein deriving at least one ventricular fill parameter comprises:
determining a minimum ventricular pressure within the fill portion;
determining a diastasis pressure within the fill portion; and
deriving a ventricular suction parameter based upon a difference between the diastasis pressure and the minimum ventricular pressure.

25. A method according to claim 21, wherein deriving at least one ventricular fill parameter comprises:
determining a ventricular diastolic pressure within the fill portion;
determining a minimum ventricular pressure with the fill portion; and
deriving a transvalve pressure gradient parameter based upon a difference between the ventricular diastolic pressure and the minimum ventricular pressure.

26. A method according to claim 21, wherein deriving at least one ventricular fill parameter comprises:
    determining $dP/dt_{min}$;
    determining ventricular pressure at a time when $dP/dt_{min}$ occurs ($P_{STI}$);
    determining ventricular pressure at a beginning of a next ventricular pumping cycle (VDP); and
    deriving an isovoumetric relaxation constant based upon $dP/dt_{min}$, $P_{STI}$, and VDP.

27. An implantable medical device comprising:
    an input circuit that receives a pressure waveform signal representative of a pressure (LVP) sensed within a left ventricle of a patient's heart as a function of time (t); and
    a processor that derives from the pressure waveform signal at least one hemodynamic parameter based upon at least one left ventricular pressure value.

28. An implantable medical device according to claim 1 and further comprising a blood pressure sensor located in the left ventricle for providing the pressure waveform signal to the input circuit.

29. An implantable medical device according to claim 27, wherein the processor derives an estimated aortic diastolic pressure based upon at least one of (a) pressure in the left ventricle at a time corresponding to a maximum rate of pressure increase ($dP/dt_{max}$), and (b) pressure in the left ventricle at a time corresponding to a maximum rate of pressure decline ($dP/dt_{min}$).

30. An implantable medical device according to claim 29, wherein the processor derives an estimated aortic systolic pressure based upon a peak pressure in the left ventricle.

31. An implantable medical device according to claim 30, wherein the processor derives an estimated aortic mean pressure based upon the estimated aortic systolic pressure and the estimated aortic diastolic pressure.

32. An implantable medical device according to claim 27, wherein the processor derives from the pressure waveform signal at least one of pre-ejection interval, systolic time interval, and an ejection duration.

33. An implantable medical device according to claim 27, wherein the input circuit also receives an electrical signal representative of electrical activity in the heart as a function of time.

34. An implantable medical device according to claim 27, wherein the processor derives from the pressure waveform signal at least one left ventricular fill parameter based upon left ventricular pressure values during a fill portion between occurrence of $dP/dt_{min}$ and the beginning of a next ventricular pumping cycle.

35. An implantable medical device according to claim 34, wherein the processor derives at least one ventricular fill parameter by:
    producing a dP/dt waveform from the pressure waveform signal;
    identifying the fill portion of the pressure waveform signal;
    identifying a diastasis portion of the fill portion using the dP/dt waveform; and
    deriving a diastasis pressure representing the left ventricular pressure waveform signal.

36. An implantable medical device according to claim 34, wherein the processor determines from the fill portion of the pressure waveform signal a left ventricular end diastolic pressure, a minimum left ventricular pressure, and a left ventricular diastasis pressure.

37. An implantable medical device according to claim 36 wherein the processor derives a left atrial kick parameter based upon a difference between the left ventricular end diastolic pressure and the left ventricular diastasis pressure.

38. An implantable medical device according to claim 36, wherein the processor derives a left ventricular suction parameter based upon a difference between the left ventricular diastasis ventricular pressure and the minimum left ventricular pressure.

39. An implantable medical device according to claim 36, wherein the processor derives a transmittal pressure gradient parameter based upon a difference between the left ventricular diastolic pressure and the minimum left ventricular pressure.

40. The implantable medical deice of claim 1, wherein the process derives an isovolumetric relaxation constant based upon $dP/dt_{min}$, a left ventricular pressure at $dP/dt_{min}$ ($LVP_{STI}$), and a left ventricular pressure at occurrence Of an R-wave (LVDP).

41. A method comprising:
    sensing left ventricular blood pressure to produce a left ventricular pressure waveform; and
    deriving at least one hemodynamic parameter based upon at least one left ventricular pressure during a left ventricular pressure waveform.

42. A method according to claim 40, wherein the left ventricular blood pressure is sensed by a blood pressure sensor located in a left ventricle.

43. A method according to claim 41, wherein deriving at least one hemodynamic parameter comprises:
    deriving an estimated aortic diastolic pressure based upon left ventricular pressure amplitude at a time when (a) $dP/dt_{min}$ occurs, or (b) $dP/dt_{max}$ occurs.

44. A method according to claim 43 and further comprising:
    deriving an estimated aortic systolic pressure based upon a maximum sensed left ventricular blood pressure.

45. A method according to claim 44, and further comprising:
    deriving an estimated aortic mean pressure based upon the estimated aortic systolic pressure and the estimated aortic diastolic pressure.

46. A method according to claim 41, wherein deriving at least one hemodynamic parameter comprises:
    deriving from the left ventricular pressure waveform at least one of a pre-ejection interval, a systolic time interval, and an ejection duration.

47. A method according to claim 41, wherein deriving at least one hemodynamic parameter comprises:
    deriving, from at least two left ventricular pressure values during a fill portion of the left ventricular pressure waveform, at least one left ventricular fill parameter.

48. A method according to claim 47, wherein deriving at least one left ventricular fill parameter comprises:
    producing a dP/dt waveform representing a first derivative of the left ventricular pressure waveform;
    identifying a fill portion of the left ventricular pressure waveform;
    identifying a diastasis portion of the fill portion using the dP/dt waveform; and
    deriving a left ventricular diastasis pressure representing the left ventricular pressure in the diastasis portion of the left ventricular pressure waveform.

49. A method according to claim 48, wherein deriving at least one left ventricular fill parameter comprises:
    determining a left ventricular end diastolic pressure within the fill portion;
    determining a left ventricular diastasis pressure within the fill portion; and deriving an atrial kick parameter based upon a difference between the left ventricular end diastolic pressure and the left ventricular diastasis pressure.

50. A method according to claim 47, wherein deriving at least one left ventricular fill parameter comprises:
   determining a minimum left ventricular pressure within the fill portion;
   determining a left ventricular diastasis pressure within the fill portion; and
   deriving a left ventricular suction parameter based upon a difference between the left ventricular diastasis pressure and the minimum left ventricular pressure.

51. A method according to claim 47, wherein deriving at least one left ventricular fill parameter comprises:
   determining a left ventricular end diastolic pressure within the fill portion;
   determining a minimum left ventricular pressure within the fill portion; and
   deriving a transmitral pressure gradient parameter based upon a difference between the left ventricular end diastolic pressure and the minimum left ventricular pressure.

Although the present invention has been described with reference to diverse embodiments, depictions, examples, and the like workers skilled in the art will recognize that changes may be made in form and detail without departing from the spirit and scope of the invention as defined in the claims appended hereinbelow.

What is claimed is:

1. An implantable medical device, comprising:
   an input circuit that receives a pressure waveform signal representative of a pressure (P) sensed within a ventricle of a patient's heart as a function of time (t); and
   a processor that derives from the pressure waveform signal at least one hemodynamic parameter based upon at least one ventricular pressure value during a portion of the pressure waveform signal between a peak ventricular pressure and a beginning of a next ventricular pumping cycle; and
   wherein the processor derives an estimated arterial diastolic pressure based upon pressure in the ventricle at a time corresponding to a maximum rate of pressure decline ($dP/dt_{min}$).

2. An implantable medical device according to claim 1 and further comprising a blood pressure sensor located in the ventricle for providing the pressure waveform signal to the input circuit.

3. An implantable medical device according to claim 2, wherein the blood pressure sensor is a right ventricular pressure sensor, and the estimated arterial diastolic pressure is an estimated pulmonary artery diastolic pressure.

4. An implantable medical device according to claim 2, wherein the blood pressure sensor is a left ventricular pressure sensor, and the estimated arterial diastolic pressure is an estimated aortic diastolic pressure.

5. An implantable medical device according to claim 1, wherein the input circuit also receives an electrical signal representative of electrical activity in the heart as a function of time.

6. An implantable medical device according to claim 1, wherein the processor derives from the pressure waveform signal at least one ventricular fill parameter based upon pressure values during a fill portion between occurrence of $dP/dt_{min}$ and the beginning of a next ventricular pumping cycle.

7. An implantable medical device according to claim 6, wherein the processor derives at least one ventricular fill parameter by:
   producing a dP/dt waveform from the pressure signal;
   identifying a fill portion of the pressure waveform signal;
   identifying a diastasis portion of the fill portion using the dP/dt waveform; and
   deriving a diastasis pressure representing the ventricular pressure in the diastasis portion of the pressure waveform signal.

8. An implantable medical device according to claim 6, wherein the processor determines from the fill portion of the pressure waveform signal a ventricular diastolic pressure, a minimum ventricular pressure, and a diastasis pressure.

9. An implantable medical device, comprising:
   an input circuit that receives a pressure waveform signal representative of a pressure (P) sensed within a ventricle of a patient's heart as a function of time (t); and
   a processor that derives from the pressure waveform signal at least one hemodynamic parameter based upon at least one ventricular pressure value during a portion of the pressure waveform signal between a peak ventricular pressure and a beginning of a next ventricular pumping cycle;
   wherein the processor determines from the fill portion of the pressure waveform signal a ventricular diastolic pressure, a minimum ventricular pressure, and a diastasis pressure;
   wherein the processor derives from the pressure waveform signal at least one ventricular fill parameter based upon pressure values during a fill portion between occurrence of $dP/dt_{min}$ and the beginning of a next ventricular pumping cycle; and
   wherein the processor derives an atrial kick parameter based upon a difference between the ventricular end diastolic pressure and the diastasis pressure.

10. An implantable medical device, comprising:
   an input circuit that receives a pressure waveform signal representative of a pressure (P) sensed within a ventricle of a patient's heart as a function of time (t); and
   a processor that derives from the pressure waveform signal at least one hemodynamic parameter based upon at least one ventricular pressure value during a portion of the pressure waveform signal between a peak ventricular pressure and a beginning of a next ventricular pumping cycle;
   wherein the processor determines from the fill portion of the pressure waveform signal a ventricular diastolic pressure, a minimum ventricular pressure, and a diastasis pressure;
   wherein the processor derives from the pressure waveform signal at least one ventricular fill parameter based upon pressure values during a fill portion between occurrence of $dP/dt_{min}$ and the beginning of a next ventricular pumping cycle; and
   wherein the processor derives a ventricular suction parameter based upon a difference between the diastasis ventricular pressure and the minimum ventricular pressure.

11. An implantable medical device, comprising:
   an input circuit that receives a pressure waveform signal representative of a pressure (P) sensed within a ventricle of a patient's heart as a function of time (t); and
   a processor that derives from the pressure waveform signal at least one hemodynamic parameter based upon at least one ventricular pressure value during a portion of the pressure waveform signal between a peak ventricular pressure and a beginning of a next ventricular pumping cycle;
   wherein the processor determines from the fill portion of the pressure waveform signal a ventricular diastolic pressure, a minimum ventricular pressure, and a diastasis pressure;

wherein the processor derives from the pressure waveform signal at least one ventricular fill parameter based upon pressure values during a fill portion between occurrence of dP/dt$_{min}$ and the beginning of a next ventricular pumping cycle; and wherein the processor derives a transvalve pressure gradient parameter based upon a difference between the ventricular diastolic pressure and the minimum ventricular pressure.

12. An implantable medical device, comprising:
an input circuit that receives a pressure waveform signal representative of a pressure (P) sensed within a ventricle of a patient's heart as a function of time (t); and
a processor that derives from the pressure waveform signal at least one hemodynamic parameter based upon at least one ventricular pressure value during a portion of the pressure waveform signal between a peak ventricular pressure and a beginning of a next ventricular pumping cycle; and
wherein the process derives an isovolumetric relaxation constant based upon dP/dt$_{min}$, a ventricular pressure at dP/dt (P$_{STI}$) and a ventricular pressure at occurrence of an R-wave (VDP).

13. An implantable medical device, comprising:
an input circuit that receives a pressure waveform signal representative of a pressure (P) sensed within a ventricle of a patient's heart as a function of time (t); and
a processor that derives from the pressure waveform signal at least one hemodynamic parameter based upon at least one ventricular pressure value during a portion of the pressure waveform signal between a peak ventricular pressure and a beginning of a next ventricular pumping cycle, wherein the processor derives an atrial kick parameter based upon a difference between ventricular end diastolic pressure and diastasis pressure.

14. An implantable medical device, comprising:
an input circuit that receives a pressure waveform signal representative of a pressure (P) sensed within a ventricle of a patient's heart as a function of time (t); and
a processor that derives from the pressure waveform signal at least one hemodynamic parameter based upon at least one ventricular pressure value during a portion of the pressure waveform signal between a peak ventricular pressure and a beginning of a next ventricular pumping cycle, wherein the processor derives a ventricular suction parameter based upon a difference between diastasis ventricular pressure and minimum ventricular pressure.

15. An implantable medical device, comprising:
an input circuit that receives a pressure waveform signal representative of a pressure (P) sensed within a ventricle of a patient's heart as a function of time (t); and
a processor that derives from the pressure waveform signal at least one hemodynamic parameter based upon at least one ventricular pressure value during a portion of the pressure waveform signal between a peak ventricular pressure and a beginning of a next ventricular pumping cycle, wherein the processor derives a transvalve pressure gradient parameter based upon a difference between ventricular diastolic pressure and minimum ventricular pressure.

* * * * *